(12) United States Patent
Spencer et al.

(10) Patent No.: US 10,113,993 B2
(45) Date of Patent: Oct. 30, 2018

(54) PHASED ARRAY SYSTEM FOR INSPECTION OF LASER WELDS

(71) Applicant: Edison Welding Institute, Inc., Columbus, OH (US)

(72) Inventors: Roger Spencer, Ashville, OH (US); Paul C. Boulware, Columbus, OH (US); Jeong K. Na, Centerville, OH (US)

(73) Assignee: Edison Welding Institute, Inc., Columbus, OH (US)

( * ) Notice: Subject to any disclaimer, the term of this patent is extended or adjusted under 35 U.S.C. 154(b) by 14 days.

(21) Appl. No.: 15/092,193

(22) Filed: Apr. 6, 2016

(65) Prior Publication Data
US 2016/0320344 A1    Nov. 3, 2016

Related U.S. Application Data

(60) Provisional application No. 62/144,118, filed on Apr. 7, 2015.

(51) Int. Cl.
  *G01N 29/26*    (2006.01)
  *G01N 29/04*    (2006.01)
  (Continued)

(52) U.S. Cl.
  CPC ......... *G01N 29/043* (2013.01); *G01N 29/262* (2013.01); *G01N 29/265* (2013.01);
  (Continued)

(58) Field of Classification Search
  CPC ................. G01N 29/075; G01N 29/24; G01N 2291/0234; G01N 2291/2672;
  (Continued)

(56) References Cited

U.S. PATENT DOCUMENTS 4,532,808 A * 8/1985 Wentzell ............ G01N 29/2487
                                                         376/249
5,370,006 A    12/1994 Zollinger et al.
(Continued)

FOREIGN PATENT DOCUMENTS

WO        2012089335 A1    7/2012

OTHER PUBLICATIONS

International Search Report and Written Opinion of the International Searching Authority received in PCT/US2016/026208, dated Jun. 24, 2016.

*Primary Examiner* — Harshad R Patel
(74) *Attorney, Agent, or Firm* — Frost Brown Todd LLC

(57) ABSTRACT

A system for non-destructively characterizing laser welds that includes at least one phased array probe that includes a plurality of ultrasonic transducer elements arranged in an array at one end of the probe, wherein the transducer elements are operative to both generate ultrasonic signals and to receive reflections thereof, wherein the transducer elements are further arranged into discrete subgroups, and wherein each subgroup may be activated independently of the other subgroups and at different time intervals; a combination of materials for allowing the probe to conform to a contoured surface of a laser weld while enabling sound energy to be transferred directly into a laser weld under test conditions, wherein the combination of materials further includes a flexible membrane mounted on the end of the probe and a fluid filled chamber material disposed between the membrane and the array of ultrasonic transducer elements; and a data processor in communication with the at least one phased array probe that includes software having at least one imaging algorithm for processing data received from the probe and generating color coded ultrasonic C-scan images of a characterized laser weld.

10 Claims, 7 Drawing Sheets

(51) Int. Cl.
  *G01N 29/265* (2006.01)
  *G01N 29/28* (2006.01)
(52) U.S. Cl.
  CPC ....... *G01N 29/28* (2013.01); *G01N 2291/044* (2013.01); *G01N 2291/106* (2013.01); *G01N 2291/267* (2013.01); *G01N 2291/2638* (2013.01)
(58) Field of Classification Search
  CPC ......... G01N 2291/0289; G01N 29/262; G01N 29/30; G01N 29/0645; G01N 2291/2638
  See application file for complete search history.

(56) References Cited

U.S. PATENT DOCUMENTS

| | | | |
|---|---|---|---|
| 6,948,369 B2 | 9/2005 | Fleming et al. | |
| 7,021,143 B2* | 4/2006 | Dasch | G01N 29/225 73/620 |
| 7,698,944 B2* | 4/2010 | Takada | G01N 29/041 73/588 |
| 7,926,349 B2* | 4/2011 | Sargent | G01N 29/041 73/588 |
| 7,984,651 B2* | 7/2011 | Randall | G10K 11/341 600/443 |
| 8,079,263 B2* | 12/2011 | Randall | G01S 7/52073 600/437 |
| 8,164,982 B2* | 4/2012 | Okuda | B06B 1/0629 367/152 |
| 8,220,334 B2* | 7/2012 | Klessel | G01S 7/52028 310/322 |
| 8,485,036 B2* | 7/2013 | Crumpton | G01N 29/043 73/622 |
| 8,499,634 B2* | 8/2013 | Urbano | A61B 8/4472 600/446 |
| 8,544,714 B1* | 10/2013 | Obaditch | B23K 20/123 228/102 |
| 8,554,328 B2* | 10/2013 | Faraji | A61N 1/375 607/54 |
| 8,600,299 B2* | 12/2013 | Randall | A61B 8/00 128/916 |
| 8,616,062 B2* | 12/2013 | Kono | G01N 29/265 73/643 |
| 8,656,783 B2* | 2/2014 | Randall | G01S 7/52028 600/447 |
| 8,746,070 B2* | 6/2014 | Tippit, Jr. | G01N 29/221 73/620 |
| 2005/0126293 A1* | 6/2005 | Dasch | G01N 29/225 73/618 |
| 2007/0157730 A1* | 7/2007 | Ochiai | F22B 37/003 73/627 |
| 2010/0064495 A1* | 3/2010 | Iizuka | G01N 29/043 29/407.01 |
| 2010/0107725 A1* | 5/2010 | Iizuka | G01N 29/11 73/1.82 |
| 2010/0286527 A1* | 11/2010 | Cannon | A61B 7/04 600/459 |
| 2011/0120223 A1* | 5/2011 | MacLauchlan | G01N 29/265 73/618 |
| 2012/0091185 A1* | 4/2012 | Ume | B23K 9/0956 228/1.1 |
| 2012/0167690 A1* | 7/2012 | Yamano | G01N 29/043 73/632 |
| 2012/0243771 A1* | 9/2012 | Matsumoto | G01N 29/0672 382/141 |
| 2012/0272739 A1* | 11/2012 | Both | G01N 29/041 73/632 |
| 2012/0310551 A1* | 12/2012 | Na | G01N 29/0645 702/39 |
| 2013/0167646 A1* | 7/2013 | Frederick | G01N 29/07 73/627 |
| 2013/0194891 A1* | 8/2013 | Kristoffersen | A61B 8/58 367/13 |
| 2013/0255384 A1* | 10/2013 | Putsherry | G01N 29/262 73/588 |
| 2013/0308419 A1* | 11/2013 | Singh | G01N 29/043 367/7 |
| 2013/0312528 A1* | 11/2013 | Feydo | G01N 29/262 73/632 |
| 2013/0319120 A1* | 12/2013 | Fetzer | G01N 29/225 73/628 |
| 2013/0338941 A1* | 12/2013 | Lin | G01N 29/348 702/39 |
| 2014/0036620 A1* | 2/2014 | Ronchi | G01S 15/8925 367/7 |
| 2014/0165730 A1* | 6/2014 | Na | G01N 29/0645 73/588 |
| 2016/0231291 A1* | 8/2016 | Boulware | G01N 29/262 |
| 2016/0320344 A1* | 11/2016 | Spencer | G01N 29/043 |

* cited by examiner

| 1 | 2 | 3 | 4 | 5 | 6 | 7 | 8 | 9 | 10 |
|---|---|---|---|---|---|---|---|---|---|
| 11 | 12 | 13 | 14 | 15 | 16 | 17 | 18 | 19 | 20 |
| 21 | 22 | 23 | 24 | 25 | 26 | 27 | 28 | 29 | 30 |
| 31 | 32 | 33 | 34 | 35 | 36 | 37 | 38 | 39 | 40 |
| 41 | 42 | 43 | 44 | 45 | 46 | 47 | 48 | 49 | 50 |
| 51 | 52 | 53 | 54 | 55 | 56 | 57 | 58 | 59 | 60 |
| 61 | 62 | 63 | 64 | 65 | 66 | 67 | 68 | 69 | 70 |
| 71 | 72 | 73 | 74 | 75 | 76 | 77 | 78 | 79 | 80 |
| 81 | 82 | 83 | 84 | 85 | 86 | 87 | 88 | 89 | 90 |
| 91 | 92 | 93 | 94 | 95 | 96 | 97 | 98 | 99 | 100 |

FIG.2

PHASED ARRAY SYSTEM FOR INSPECTION OF LASER WELDS

CROSS-REFERENCE TO RELATED APPLICATIONS

This patent application claims the benefit of U.S. Provisional Patent Application Ser. No. 62/144,118 filed on Apr. 7, 2015 and entitled "Matrix Phased Array System for Inspection of Laser Welds," the disclosure of which is hereby incorporated by reference herein in its entirety and made part of the present U.S. utility patent application for all purposes.

BACKGROUND OF THE INVENTION

The present invention relates in general to inspection systems and devices for use in assessing the performance of industrial manufacturing processes, and more specifically to a nondestructive inspection or evaluation system for assessing the quality of welds created by laser beam welding.

Laser beam welding is a welding technique for joining multiple pieces of metal through the use of one or more lasers. A laser beam provides a concentrated heat source that allows for the creation of narrow, deep welds at high welding rates. The laser welding process is frequently used in high-volume applications. Similar to electron beam welding, laser beam welding has a high power density (on the order of 1 MW/cm$^2$) resulting in small heat-affected zones as well as high heating and cooling rates. The spot size of the laser used in this process typically varies between 0.2 mm and 13 mm, though only smaller sizes are used for welding. The depth of penetration is proportional to the amount of power supplied, but is also dependent on the location of the focal point of the laser. Weld penetration is maximized when the focal point is slightly below the surface of the workpiece. Continuous or pulsed laser beams may be used depending upon the application. Millisecond-long pulses are typically used to weld thin materials such as razor blades while continuous laser systems are employed for deep welds.

Laser beam welding is a versatile process that is capable of welding carbon steels, HSLA steels, stainless steel, aluminum, and titanium. Resultant weld quality is high, similar to that of electron beam welding, and the speed of welding is proportional to the amount of power supplied, but also depends on the type and thickness of the workpieces. The high power capability of gas lasers make them especially suitable for high volume applications. Laser beam welding is particularly dominant in the automotive industry. However, due to high cooling rates, cracking is a concern when welding high-carbon steels, and welds created by laser beam welding must often be evaluated for weld integrity.

Acoustic methods are commonly used nondestructive testing methods for various inspection applications. Unlike other nondestructive testing methods, acoustic methods provide both surface information and internal information with regard to the welds being evaluated. Moreover, acoustic methods allow for deeper penetration into specimens and higher sensitivity to small discontinuities in a weld joint. Acoustic methods, however, do have certain limitations. The most significant limitations include the requirement of a skillful operator for using the testing device and analyzing acoustic data, as well as the very subjective nature of identifying an inadequate bond or faulty weld joint. Accordingly, the field of ultrasonic nondestructive evaluation (NDE) is in need of a reliable process or technique for identifying poor quality joints in a manner that eliminates the involvement of a skilled operator and the subjective interpretation of test data.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first system for non-destructively characterizing laser welds is provided. This first system includes at least one phased array probe, wherein the at least one phased array probe includes a plurality of ultrasonic transducer elements arranged in an array at one end of the probe, wherein the transducer elements are operative to both generate ultrasonic signals and to receive reflections thereof, wherein the transducer elements are further arranged into discrete subgroups, and wherein each subgroup may be activated independently of the other subgroups and at different time intervals; a combination of materials for allowing the probe to conform to a contoured surface of a laser weld while enabling sound energy to be transferred directly into a laser weld under test conditions, wherein the combination of materials further includes a flexible membrane mounted on the end of the probe and a fluid filled chamber or solid sound delay material disposed between the membrane and the array of ultrasonic transducer elements; and a data processor in communication with the at least one phased array probe, wherein the data processor includes software that includes at least one imaging algorithm for processing data received from the probe and generating color coded ultrasonic C-scan images of a characterized laser weld.

In accordance with another aspect of the present invention, a second system for non-destructively characterizing laser welds is provided. This second system includes at least one phased array probe, wherein the at least one phased array probe includes one hundred transducer elements arranged in an array at one end of the probe, wherein the transducer elements are operative to both generate ultrasonic signals and to receive reflections thereof, wherein the transducer elements are further arranged into discrete subgroups of 3×3 or 5×2 transducer elements, and wherein each subgroup may be activated independently of the other subgroups and at different time intervals; (ii) a combination of materials for allowing the probe to conform to a contoured surface of a laser weld while enabling sound energy to be transferred directly into a laser weld under test conditions, wherein the combination of materials further includes a flexible membrane mounted on the end of the probe and a fluid filled chamber or solid sound delay material disposed between the membrane and the array of ultrasonic transducer elements; and a data processor in communication with the at least one phased array probe, wherein the data processor includes software that includes at least one imaging algorithm for processing data received from the probe and generating color coded ultrasonic C-scan images of a characterized laser weld.

In yet another aspect of this invention, a third system for non-destructively characterizing laser welds is provided. This third system includes at least one phased array probe, wherein the at least one phased array probe includes one hundred transducer elements arranged in an array at one end of the probe, wherein the transducer elements are operative to both generate ultrasonic signals and to receive reflections thereof, wherein the transducer elements are further arranged into discrete subgroups of 3×3 or 5×2 transducer elements, and wherein each subgroup may be activated independently of the other subgroups and at different time intervals; a combination of materials for allowing the probe to conform to a contoured surface of a laser weld while enabling sound energy to be transferred directly into the laser weld under test conditions, wherein the combination of materials further includes a flexible membrane mounted on the end of the probe and a fluid filled chamber or solid sound delay material disposed between the membrane and the array of ultrasonic transducer elements; a data processor in communication with the at least one phased array probe, wherein the data processor includes software that includes at least one imaging algorithm for processing data received from the probe and generating color coded ultrasonic C-scan images of a characterized laser weld; and a fixture adapted to be mounted on a robot or other mechanical actuator for retaining the at least one phased array probe, wherein the fixture includes a slide, wherein the slide provides compliance for accommodating variations in welded part shape and location, and wherein the compliance allows the probe to be applied to a weld surface to be inspected with a predetermined force that is constant across a predetermined range of displacements.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein:

FIG. 2 is a simplified illustration of the plurality of ultrasonic transducer elements arranged in an array at one end of the probe of FIG. 1, wherein a predetermined group of ultrasonic transducer elements are operating in combination with one another in a predetermined manner;

DETAILED DESCRIPTION OF THE INVENTION

Figure 1:
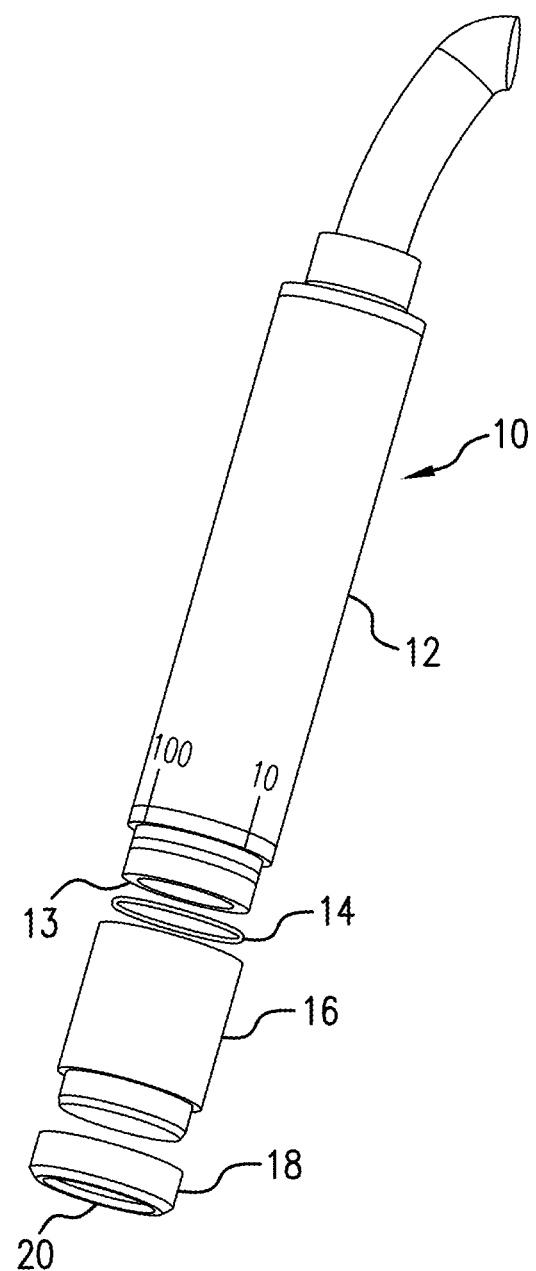
FIG. 1 provides an exploded perspective view of an ultrasonic probe in accordance with an exemplary embodiment of the present invention.

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present application incorporates by reference herein U.S. patent application Ser. No. 12/186,047 (U.S. Pat. No. 8,215,173); Ser. No. 13/468,502 (U.S. Pat. No. 9,063,059); and Ser. No. 14/183,643 (U.S. Pat. No. 9,037,419); in their entirety, for all purposes. With regard to the nomenclature used herein, the present invention is described as being useful for analyzing the integrity of laser welds between a first and second workpiece or upper and lower sheets of metal. However, this invention is applicable to all welds regardless of material, configuration, or the number of workpieces. Thus, while the present disclosure generally refers to a laser welds, one skilled in the art will appreciate that the present invention detects stuck portions of joints, which are often referred to as kissing bonds or weak bonds in the field of adhesives. This invention is also applicable to metals and nonmetals alike and is not limited to laser welding, but some embodiments may also be used to examine solid state welds, brazed and soldered joints. Thus, while this method has particular application in the automated analysis of laser welds, it may also be used to evaluate continuous bonds.

A stuck weld or stuck joint occurs when workpieces (e.g., pieces of sheet metal) are held together by localized fusion at the welding interface, but no acceptable weld has formed as a result of the welding process. A stuck weld typically results from heat at the welding interface being insufficient to create an acceptable weld. In the absence of a properly formed weld, fusion may occur at certain points of contact between the sheets of metal. With coated materials, coatings can melt and refreeze, effectively soldering the parts together. The resulting bonds are often strong enough to hold the workpieces together under light loads, but reasonable force will pull them apart. If ultrasonic testing is used to analyze weld integrity, transmitted ultrasonic beams (i.e., sound waves) will not pass through the interface between sheets if no fusion has occurred. If a stuck weld as occurred, resulting in fusion, transmitted ultrasonic beams will pass partially though the sheet interface. If a weld has been properly formed, transmitted ultrasonic beams will pass completely through the sheet interface.

Phased Array Ultrasonic Testing (PAUT) may be used for flaw detection, sizing, and imaging. PAUT technology includes the ability to electronically modify the characteristics of an acoustic probe. Probe modifications are performed by introducing time shifts in the signals sent to (pulse) and received from (echo) individual elements of an array probe. Three common formats for collecting and displaying ultrasonic data for purposes of non-destructive evaluation are A-scan, B-scan and C-scan presentations. Each presentation mode provides a means for visualizing and evaluating the region of material being inspected. An A-scan is a simple RF waveform presentation showing the time and amplitude of an ultrasonic signal, as commonly provided by conventional ultrasonic flaw detectors and waveform display thickness gages. An A-scan is an amplitude modulation scan, and as generally applied to pulse echo ultrasonics, horizontal and vertical sweeps are proportional to time or distance and amplitude or magnitude respectively. Thus the location and magnitude of acoustical interface are indicated as to depth below the transducer. The relative amount of energy received is plotted along the vertical axis, and the elapsed time (which may be related to the sound energy travel time within the material) is displayed along the horizontal axis. Most instruments utilizing an A-scan display allow the signal to be displayed in its natural radio frequency form (RF) as a fully rectified RF signal or as either the positive or negative half of the RF signal. In the A-scan presentation, relative discontinuity size can be estimated by comparing the signal amplitude obtained from an unknown reflector to that from a known reflector. Reflector depth can be determined by the position of the signal on the horizontal sweep. In this invention, a C-scan from a phased array system involves generating electronic scans of the x-axis and y-axis using a two dimensional array. Signal amplitude or depth data is collected within gated regions of interest. Data is plotted with each focal law progression, using the programmed beam aperture. Utilizing a linear or matrix phased array probe, beam steering can be accomplished in multiple directions.

The present invention reduces in-plant destructive testing of laser welds as part of laser welding process quality control, thereby saving time and money. This technology also provides in-field testing on suspected non-conforming laser welds. Appropriate algorithms and signal processing are important aspects of this invention. With regard to the visualization component of this invention when moving from element to element within the probe array, the image changes; thus, this invention includes one or more algorithms that assign color in a predetermined manner. With regard to the probe component, the laser probe may be a 2-dimensional probe that includes a relatively flat, but flexible membrane, which improves acoustic coupling between the probe and the part being evaluated compared to probes that do not include a flexible membrane. In other embodiments, one-dimensional linear probes or three-dimensional curved probes are used. Probe design typically includes a body or columnar housing, a water column, and a flexible membrane, which accommodates the non-smooth surface of the laser weld and prevents the probe from rocking back and forth over the part being analyzed. The mid-tube portion of the probe component of the preset invention (see FIG. 1) is roughly half the physical length of the probe described in U.S. patent application Ser. No. 13/468,502 (U.S. Pat. No. 9,063,059); and Ser. No. 14/183,643 (U.S. Pat. No. 9,037,419).

Figure 3:
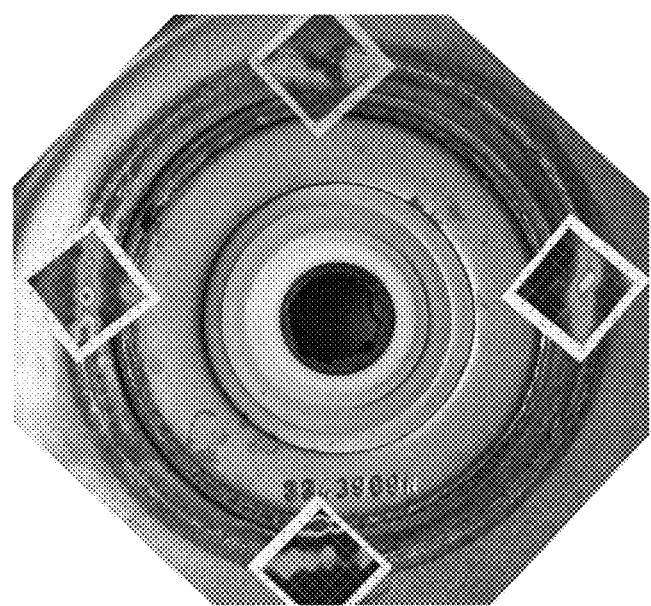
FIG. 3 is a photograph of a manufactured part that includes laser welds that are being nondestructively evaluated with the system and device of the present invention, wherein C-scans of the area of the analyzed weld are overlaid on the photograph for purposes of illustrating the visual output of the system of this invention.
Figure 4:
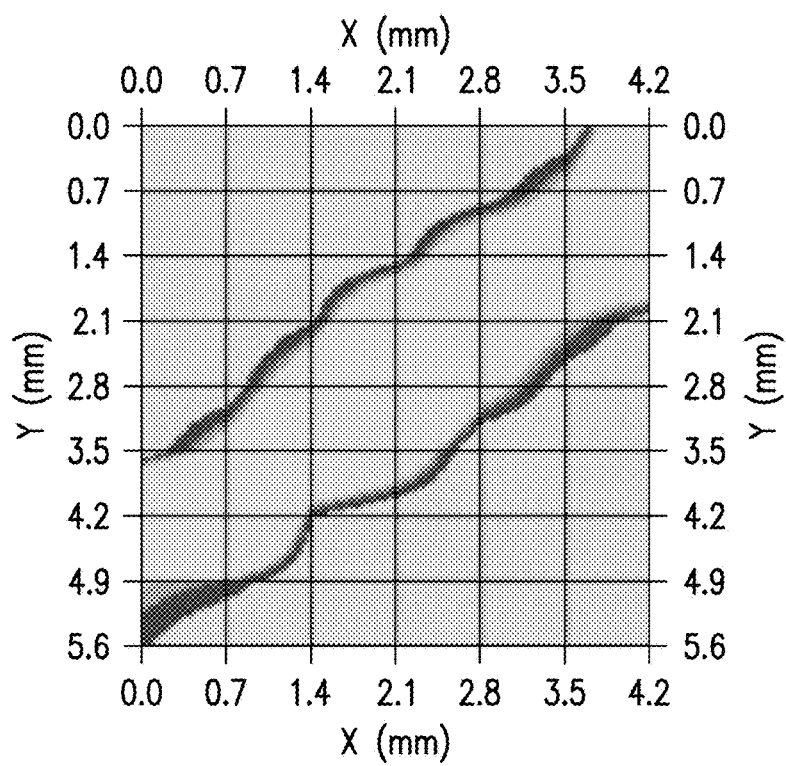
FIG. 4 is a screen capture of a C-scan generated by the system and device of the present invention when a laser weld is being evaluated and wherein the entire area visible represents the welded region of a part, and wherein the central diagonal section, which is typically presented in red, represents the actual laser weld.
Figure 5:
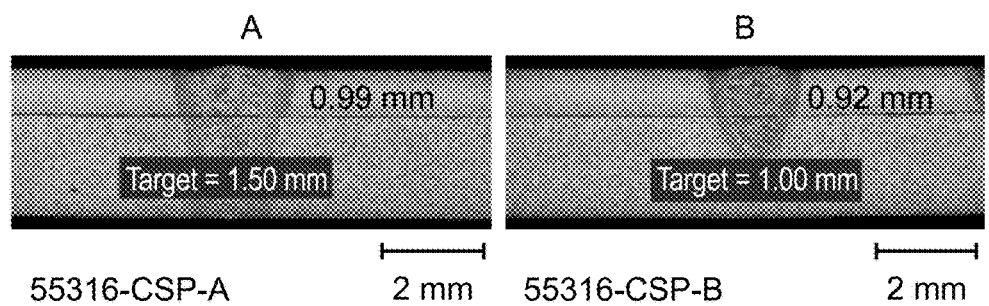
FIG. 5 provides photographs illustrating the appearance of laser welds suitable for evaluation with the system and device of the present invention.
Figure 6:
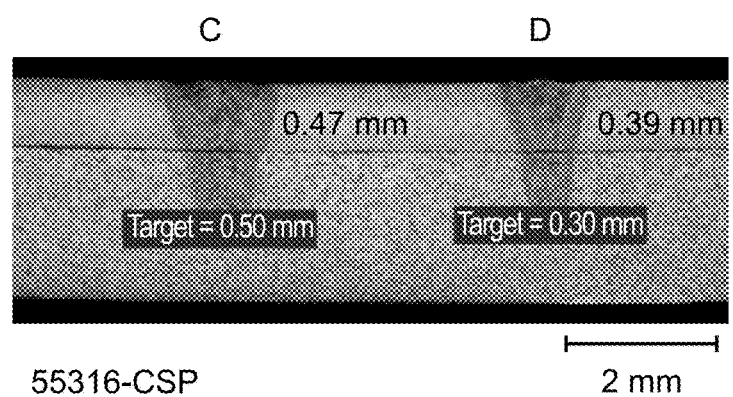
FIG. 6 provides an additional photograph illustrating the appearance of laser welds suitable for evaluation with the system and device of the present invention.

FIG. 1 provides an exploded perspective view of an ultrasonic probe in accordance with an exemplary embodiment of the present invention, wherein probe 10 includes upper portion 12, transducer array 13, O-ring 14, mid-tube portion 16, probe cap 18, and flexible membrane 20. FIG. 2 is a simplified illustration of the plurality of ultrasonic transducer elements arranged in an array at one end of the probe of FIG. 1, wherein a predetermined group of ultrasonic transducer elements are operating in combination with one another in a predetermined manner. In an exemplary embodiment, the laser weld evaluation system is expanded from 64 to 100 (10×10) ultrasonic transducer elements and the pitch of each ultrasonic transducer element is reduced to produce a smaller ultrasonic beam for determining the width of a weld at the fusion of two sheets of metal in a lap weld, wherein the top sheet of metal is typically thinner than the bottom sheet (see FIGS. 5-6). In this embodiment, the probe elements are grouped, and 8-10 elements are fired at a time for evaluating laser welds, as opposed to firing single elements for the evaluation of resistance spot welds or other weld types. In some embodiments, groupings of 3×3 or 5×2 elements permit electronic focusing of the ultrasonic beam down into the relatively thin area of a laser weld. The ultrasonic beam of a single element diverges, which is an important aspect of phased array. In this invention, the elements are grouped and each element of the group is indexed one element at a time. The group of elements is then fired and a reading is taken. Further indexing occurs until the entire aperture is indexed and an accumulation of all elements is achieved. FIG. 3 is a photograph of a part that includes laser welds that are being evaluated with the system and device of the present invention, wherein C-scans of the area of the weld are overlaid on the photograph for purposes of illustrating the visual output of the claimed system. FIG. 4 is a screen capture of a C-scan generated by the system and device of the present invention when a laser weld is being evaluated and wherein the visible entire area represents the welded region of a part, and wherein the central diagonal section, which is typically presented in red, represents the actual laser weld. The area outside of the central diagonal region is typically presented in blue, and the red and blue regions together represent the entire welded area. This invention has been successfully tested on lap joint laser welds having a nominal interface weld width of approximately 1 mm. Testing has also been conducted on two sheet stackups of carbon steel sheet material. A 32-channel board is typically used and software measurement of the weld width provides rapid, repeatable results.

The present invention also provides a system and method for assisting an operator in holding ultrasonic probe 10 normal to an inspected surface. The signal time from individual elements or groups of elements on either side of the weld being analyzed is monitored, and when these elements detect a time that is generally equal, the system determines the ultrasonic probe to be normal to the surface being analyzed. This aspect then ties to an auto-capture function of the invention. The inspection of a laser weld is basically the inspection of the width of the weld. The length of the weld is undetermined and can be, in theory, of infinite dimension. By moving the probe, the system inspects along the length of a weld of undefined length and determines its width.

In various embodiments of this invention, a computerized controller is coupled to the acoustic probe and transducer elements for directing transmission of the ultrasonic signals and for summing and receiving responses therefrom. The controller is operative to: (i) generate and acquire acoustic signals; (ii) detect the surface of the laser weld for each element grouping; (iii) adjust instrument gating to compensate for surface profile and differences in probe orientation; (iv) measure the signal amplitude ratio between responses reflected from the unbonded areas and areas with good bond; (v) recognize a subset of the responses as being reflected from the un-bonded areas associated with the laser weld and to separate the subset from a remainder of the responses; (vi) measure the extent of the non-delamination dimensions; and (vii) present a two-dimensional color coded image of non-delamination of the laser weld. In summary, some of the distinct advantages of this invention include: (i) a one, two, or three-dimensional matrix probe having an array of ultrasonic transducer elements; (ii) a phase delay within groups of sub-elements to form ultrasonic beam focusing and steering capability; (iii) a conformable ultrasonic probe membrane (no need for an attenuation correction); and (iv) an imaging process that utilizes electronic gates to filter out unwanted acoustic reflections.

Figure 7:
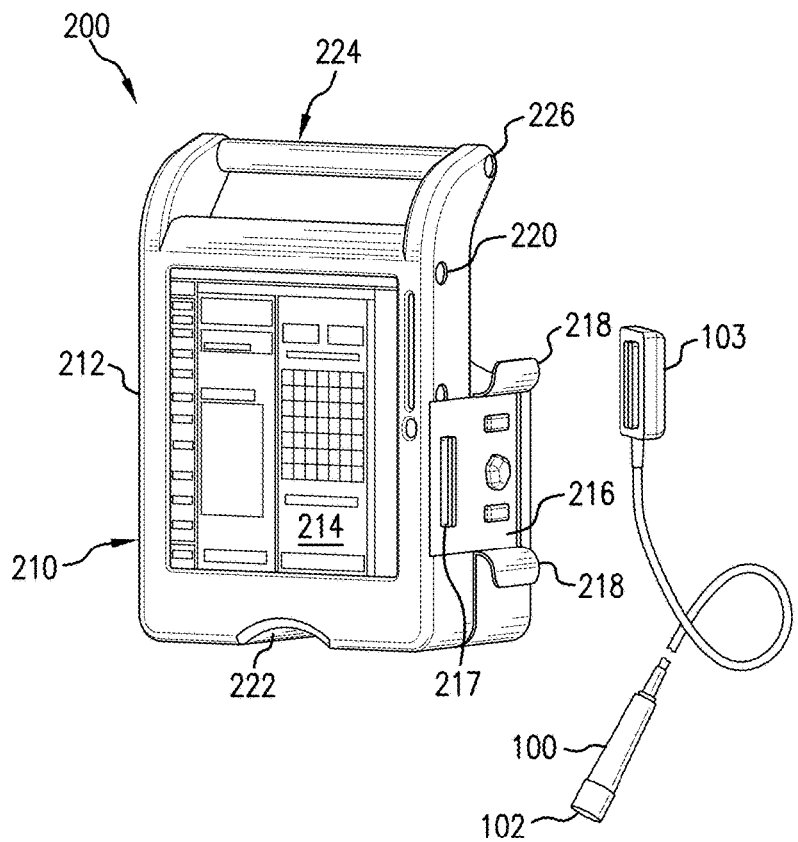
FIG. 7 is a front perspective view of a portable system for non-destructively characterizing laser welds, in accordance with an exemplary embodiment of this invention.
Figure 8:
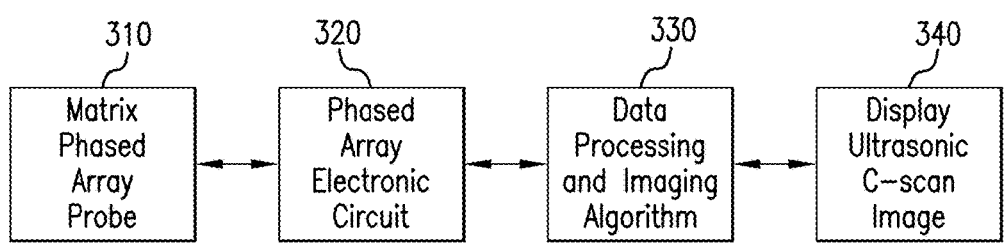
FIG. 8 is a block diagram of the basic functionality of the system of FIG. 7.

With reference to FIGS. 7-8, in one exemplary embodiment, the present invention is assembled into a fully-integrated, portable (i.e., hand-held), battery-operated, non-destructive inspection system that reduces or eliminates the need for destructive testing of parts and components that include laser welded joints. This unit includes ultrasonic phased array circuitry that is lower in cost, smaller in size, and has the capability of being battery operated so that the device is cost effective and portable for usage on a production line. Thus, the system can be used as a tool for checking the integrity of welded products with great cost-saving and efficiency. This system, which may be referred to as "EWI SpotSight®" utilizes phased array ultrasonic imaging technology to accurately assess the condition of a joint area by visualizing an ultrasonic C-scan image of the inspection area while providing real-time feedback. This system can be utilized in a wide variety of manufacturing settings for inspection of parts and components made of metals and non-metals. The system is effective for evaluating the quality of various joining configurations including laser welds and other weld types. This invention is particularly useful for the automotive and aerospace industries with regard to evaluating the quality of laser welded components parts.

As shown in FIG. 7, the portable version of this invention is intended for use as an inspection system in one or more production environments. The basic components of this system include: (i) ultrasonic phased array transmitting and receiving circuitry; (ii) a fully-integrated computer with data processing capabilities and imaging algorithm(s); (iii) at least one phased array probe having a quick connect/disconnect electrical connection; and (iv) an ergonomically designed and fully portable case with a carrying handle that provides a safe storage space for the phased array probe therein. As shown in FIG. 7, an exemplary embodiment of portable laser weld joint inspection unit 200 includes body 210 and handle 224. Body 210 further includes power switch 212, side access for USB and external monitor connections; screen 214, aluminum plate 216, connector adaptor 217 (e.g., Hypertronix or Omni Connector adaptor); cord wrap 218, stylus storage area 220, and arm rest 222. Handle 224 further includes probe storage area 226. Probe 100 is connected to probe connector 103 (e.g., multi-pin Omni connector), which then connects to weld joint inspection unit 200 at connector adapter 217. In various exemplary embodiments, the ultrasonic phased array transmitting and receiving circuitry further includes 128-channel phased array circuitry with 32-channel simultaneous multiplexing capability; the computer includes an Intel i7 dual-core powered ruggedized tablet computer running on Windows 7 or Windows 8 (or higher) operating software with a flat touch screen display that improves inspection speed by eliminating the need for a computer mouse and keyboard in a production environment; the imaging algorithm(s) further includes SpotSight® imaging software (EWI, Inc.; Columbus, Ohio) for providing the appropriate imaging algorithm(s) to process the data from the phased array electronics; the at least one matrix phased array probe further includes a 100-element 2-D matrix phased array probe (1-D or 3-D probes may be included or substituted); and the ergonomic casing further includes all features necessary for allowing cooling for the internal electronics, a handle from carrying the instrument, and various features that allow safe storage of the probe and access to all required power and data ports. Wireless connectivity (e.g., Bluetooth, Wi-Fi, cellular network, etc.) and a rechargeable battery are also typically included. The aforementioned aspects of this embodiment effectively confer the following advantageous features to the present invention: (i) the ability to quantitatively assess welds and other types of materials joining with numerical data displayed on the screen; (ii) self-contained non-destructive ultrasonic inspection system; (iii) hand-held portability; (iv) battery power; (v) touch screen and wireless functionalities; and (vi) robust quick electrical/mechanical connection of the ultrasonic probe to the unit.

FIG. 8 provides a system block diagram that illustrates the basic functionality of an exemplary embodiment of portable weld joint inspection unit 200. In this embodiment, phased array electronic circuit 320 activates matrix (or linear) phased array probe 310 with an activation command from the data processing software. Next, ultrasonic signals detected by phased array probe 310 are fed to imaging algorithm 330 to be processed for fused and non-fused conditions of joining area under inspection. Finally, color coded ultrasonic C-scan image 340 is displayed on the screen with additional numerical data such as average fused width of the weld. EWI SpotSight® software processes ultrasonic signals as they are detected by the individual subgroups of the probe array using various gates, one for the front or back surface reflection and the other for interface reflection. An ultrasonic C-scan image is plotted as raw ultrasonic data is processed real time with the dual gate imaging algorithm. The feedback time to the operator is fraction of a second and adjustment of the probe is relatively easy and fast compared to systems for which the probe has to be repositioned if results are unsatisfactory. Despite these advantages, in examining various welds, several factors can cause undesired variations including: (i) the changing acoustic impedance of an aging membrane; (ii) natural degradation of piezoelectric elements included in the sensor/probe; (iii) slight differences between transducers; and (iv) a natural tendency of the system to undersize all welds. To compensate for these variables, some embodiments of this invention include a feature that allows the ratio between the first image gate and the second image gate to be adjusted. This feature gives an operator of the system the ability to calibrate the system to welds of known weld size, thereby increasing the overall accuracy of the system. To accomplish this, the system operator places the probe on a standard which includes a weld having a known or predetermined size. If the image reads slightly larger or smaller than the standard, then the gate ratio is adjusted by the operator through specific inputs in the software. The image appearing on the screen of portable weld joint inspection unit 200 is created essentially by comparing the signal strength from the first gate to the strength from the second gate.

Figure 9:
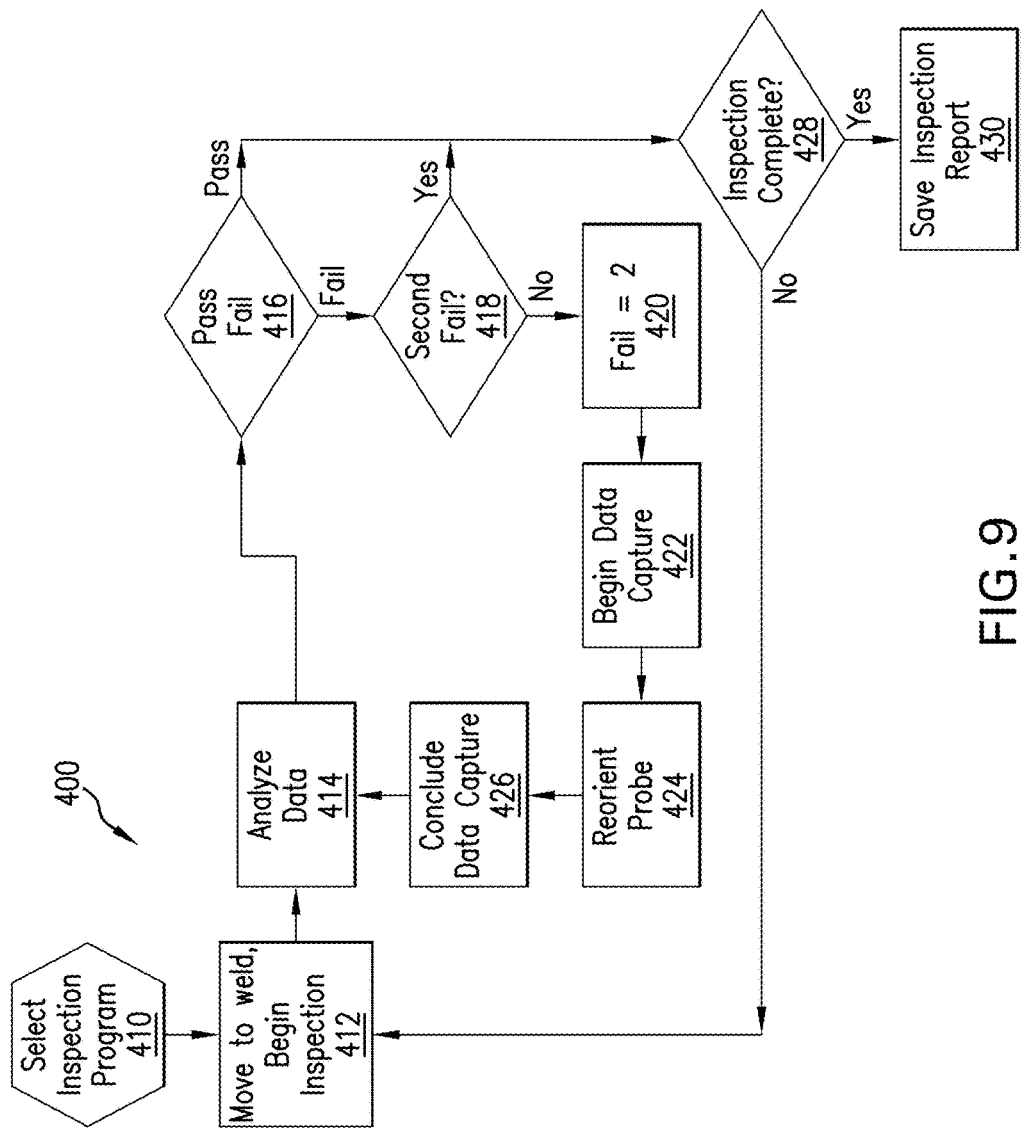
FIG. 9 provides a flow chart depicting the manner in which an automated version of the system of the present invention permits further action based on evaluation of pre-determined criteria of scan verdicts.
Figure 10:
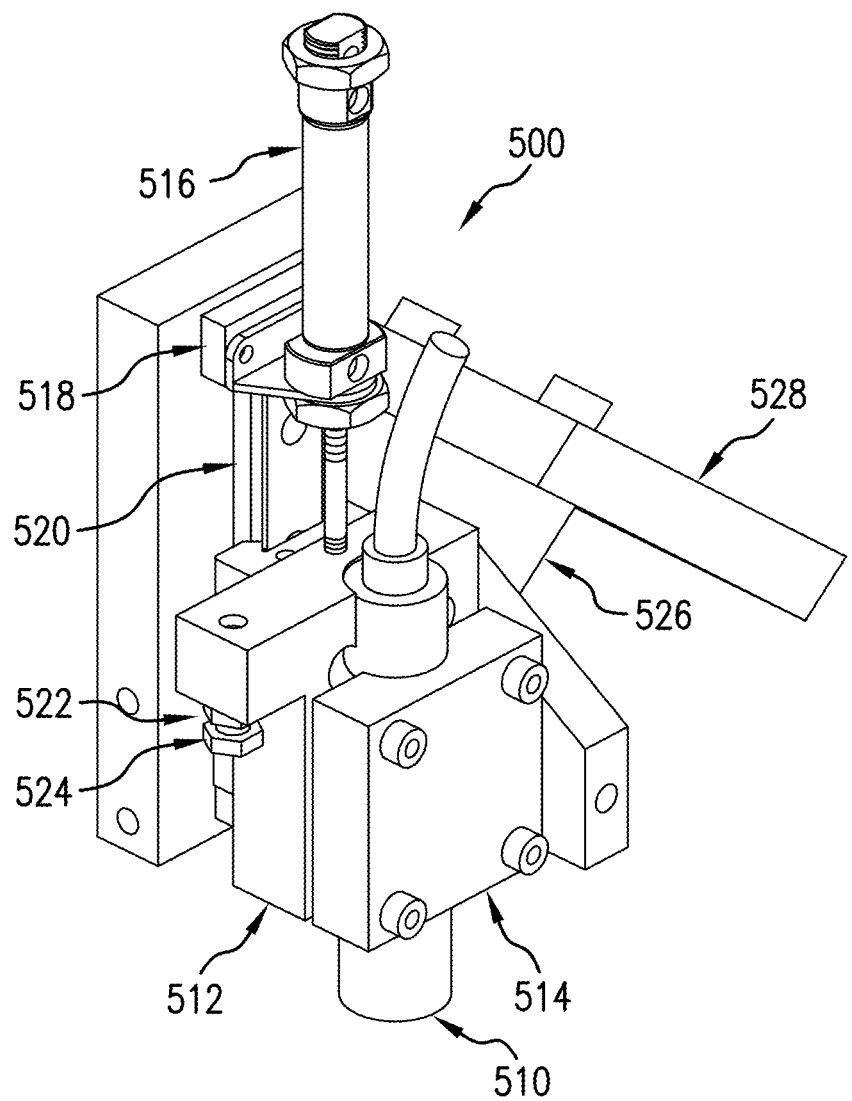
FIG. 10 is a perspective view of the probe-retaining fixture component of an exemplary automated embodiment of the present invention.

With reference to FIGS. 9-10, the present invention may be configured for manual operation or as a fully automated system. The manual configuration involves manual operation of the inspection probe as well as operation of the user interface. This embodiment relies on the operator of the system for locating the weld to be characterized and then physically manipulating the probe to provide an adequate scan for evaluation. In preparation for inspection, an operator also selects specific parameters for each individual weld and then monitors probe feedback to identify an acceptable scan before capturing a suitable image for actual evaluation. Because the system is typically used to inspect a large number of welds, manual inspection of every weld by an operator is likely to be inefficient and impractical. Accordingly, the automated version of this invention permits inspection of numerous welds with reduced or eliminated operator input by automating many of the tasks of the operator. The automated embodiment permits inspection parameters to be selected remotely based on electronic input from control equipment. In this embodiment, inspection parameters for different metal thicknesses, alloys, layers of stackup, or other relevant conditions may be selected for inspection without input from an operator. Additionally, parameters can be changed as needed for each weld, and for each different workpiece that is inspected.

Regarding motion and signal capture/analysis, a single path sequence is utilized, once the probe is placed on the weld, scanning occurs. However, if the proper scan isn't recognized, a second programmable motion is utilized. The probe is placed on a weld by means of a mechanical actuator, which is further capable of rotating the probe around the point of contact in order to vary the angle of the probe to the work surface. On initial contact, an inspection "scan" is completed, wherein each probe element is triggered, and resultant ultrasonic measurement data from each element is used to construct a C-scan image or output data representing information of the type contained in a C-scan. The C-scan image displays (or the outputted data represents) regions of successful welding, where the weld penetrates all layers of the workpiece, as well as areas where penetration is not complete. At least one algorithm evaluates measurement data to construct an outline of the weld, then determines characteristics of the weld, taking into account the measured perpendicularity of the probe to the workpiece, measured outline of the weld, and internal voids. Software delivers a pass/fail signal based on pre-determined, operator defined criteria of weld, including maximum or minimum width, cross-sectional area, perimeter, shape, or inclusion of voids. The pass/fail conclusion is then used to evaluate the need for further inspection. In the event further inspection is warranted, the system manipulates the probe through additional positions likely to produce scans of the part which better represent the condition of the weld. All of these additional scans are stored for further evaluation. At the completion of the additional moves, all captured scans are evaluated in the same way as the first scan, and a pass/fail "verdict" established for each one. The system allows further action based on evaluation of pre-determined criteria of scan verdicts. Measured weld characteristics, including but not limited to weld width, are made available for pass/fail decisions, and storage in an external disk drive or other storage medium.

FIG. 9 provides a flow chart depicting a specific exemplary process/method 400 by which the automated version of this system permits further action based on evaluation of pre-determined criteria of scan verdicts. In this example, an inspection program is selected at step 410, the probe is moved to the weld and inspection begins at step 412, weld data is analyzed at step 414, and a pass/fail determination is made. If the inspected weld passes, the system moves on to completion of the process at step 428 and an inspection report is generated and saved at step 430. If the inspected weld fails at step 416, a second fail determination is made at step 418. If the inspected weld fails a second time at step 418, the system moves on to completion of the process at step 428 and an inspection report is generated and saved at step 430. If the inspected weld does not fail a second time at step 418, a determination that further inspection is needed is made at step 420. Data capture then begins at step 422, the ultrasonic probe is reoriented at step 424, data capture is concluded at step 426, and data analysis begins again at step 414 until a determination of weld quality is eventually completed.

In the automated embodiment, the inspection probe is placed on a weld joint by means of a pneumatic cylinder, robotic actuator, or other mechanical device; thereby eliminating the need for a human operator to manually move the probe from weld to weld. Using external commands, the ultrasonic elements in the probe are activated and images (i.e., scans) of the weld being inspected are generated. For the purpose of duplicating the function of an operator manipulating the probe in search of an acceptable scan, an automated actuator moves the probe through a range of positions likely to produce acceptable results. Scan data and images generated during the search are saved for further processing and upon receiving an external command the system reviews captured images according to criteria that are based on automatically selected inspection parameters. Exemplary characteristics to be reviewed may include measured width of a weld at various locations; total area of weld penetration; weld perimeter; weld shape; or combinations thereof. Also relevant is measured normality to workpiece surface based on reflections of ultrasonic signals at disparate elements in the probe. Selected data is evaluated for quality of the weld joint and measured weld quality can be used for additional inspection of an even wider range of moves, or to label a weld as acceptable or unacceptable.

In an exemplary embodiment, the automated version of the present invention includes a probe mounted on or retained by a device, referred to herein as "fixture" having a slide that provides compliance necessary for accommodating variations of part shape and location. This compliance allows the probe to be applied to the surface to be inspected with a known force, which is constant across a wide range of displacements. Pressure is also controllable, as the inspection probe utilizes pressure within a specific range. The travel extends far enough to prevent damage to the probe in the event of a collision. With reference to FIG. 10, an exemplary embodiment of the present invention includes fixture 500, which retains ultrasonic probe 510, and that further includes a slide having probe cradle 512, clamp block 514, compliant cylinder 516, linear rail, cylinder spacer 518, assembly 520, travel stop 522, fastener 524, frame 526, and mounting flange 528.

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described.

Accordingly, departures may be made from such details without departing from the spirit or scope of the general inventive concept.

What is claimed:

1. A system for non-destructively inspecting laser welds, comprising:
   (a) at least one phased array probe, wherein the at least one phased array probe includes:
      (i) one hundred transducer elements arranged in a two-dimensional array at one end of the probe,
         a) wherein the transducer elements are operative to both generate ultrasonic signals and to receive reflections thereof,
         b) wherein the transducer elements are further arranged into discrete subgroups of 3×3 or 5×2 transducer elements, and
         c) wherein each subgroup may be activated independently of the other subgroups and at different time intervals;
      (ii) a combination of materials for allowing the probe to conform to a contoured surface of a laser weld while enabling sound energy to be transferred directly into the laser weld under test conditions, wherein the combination of materials further includes a flexible membrane mounted on the end of the probe and a fluid filled chamber or solid sound delay material disposed between the membrane and the array of ultrasonic transducer elements;
   (b) a data processor in communication with the at least one phased array probe, wherein the data processor includes software that includes at least one imaging algorithm for processing data received from the probe and generating color coded ultrasonic C-scan images of a inspected laser weld.

2. The system of claim 1, wherein activating each subgroup independently of the other subgroups and at different time intervals for each transducer element in the subgroup provides signal focusing and steering capability to the at least one phased array probe.

3. The system of claim 1, wherein the system is configured as a hand-held portable system.

4. The system of claim 1, wherein the system is configured as an automated system.

5. The system of claim 4, wherein the system includes a fixture adapted to be mounted on a robot or other mechanical actuator for retaining the at least one phased array probe.

6. The system of claim 5, wherein the robot or other mechanical actuator is operative to move the probe through a predetermined range of positions, and wherein the predetermined range of positions is operative to facilitate production of high-integrity scans of welds being inspected.

7. The system of claim 5, wherein the fixture includes a slide, and wherein the slide provides compliance for accommodating variations in welded part shape and location, and wherein the compliance allows the probe to be applied to a weld surface to be inspected with a predetermined force that is constant across a predetermined range of displacements.

8. An automated system for non-destructively inspecting laser welds, comprising:
   (a) at least one phased array probe, wherein the at least one phased array probe includes:
      (i) one hundred transducer elements arranged in a two-dimensional array at one end of the probe,
         a) wherein the transducer elements are operative to both generate ultrasonic signals and to receive reflections thereof,
         b) wherein the transducer elements are further arranged into discrete subgroups of 3×3 or 5×2 transducer elements, and
         c) wherein each subgroup may be activated independently of the other subgroups and at different time intervals;
      (ii) a combination of materials for allowing the probe to conform to a contoured surface of a laser weld while enabling sound energy to be transferred directly into the laser weld under test conditions, wherein the combination of materials further includes a flexible membrane mounted on the end of the probe and a fluid filled chamber or solid sound delay material disposed between the membrane and the array of ultrasonic transducer elements;
   (b) a data processor in communication with the at least one phased array probe, wherein the data processor includes software that includes at least one imaging algorithm for processing data received from the probe and generating color coded ultrasonic C-scan images of a inspected laser weld; and
   (c) a fixture adapted to be mounted on a robot or other mechanical actuator for retaining the at least one phased array probe, wherein the fixture includes a slide, wherein the slide provides compliance for accommodating variations in welded part shape and location, and wherein the compliance allows the probe to be applied to a weld surface to be inspected with a predetermined force that is constant across a predetermined range of displacements.

9. The system of claim 8, wherein activating each subgroup independently of the other subgroups and at different time intervals for each transducer element in the subgroup provides signal focusing and steering capability to the at least one phased array probe.

10. The system of claim 8, wherein the robot or other mechanical actuator is operative to move the probe through a predetermined range of positions, and wherein the predetermined range of positions is operative to facilitate production of high-integrity scans of welds being inspected.

* * * * *